(12) United States Patent
Radhakrishnan et al.

(10) Patent No.: US 12,033,320 B2
(45) Date of Patent: Jul. 9, 2024

(54) METHODS, SYSTEMS, AND DEVICES FOR ANALYZING LUNG IMAGING DATA TO DETERMINE COLLATERAL VENTILATION

(71) Applicant: Pulmonx Corporation

(72) Inventors: Sri Radhakrishnan, Cupertino, CA (US); Ryan Olivera, Granite Bay, CA (US)

(73) Assignee: Pulmonx Corporation, Redwood City, CA (US)

( * ) Notice: Subject to any disclaimer, the term of this patent is extended or adjusted under 35 U.S.C. 154(b) by 197 days.

(21) Appl. No.: 17/444,336

(22) Filed: Aug. 3, 2021

(65) Prior Publication Data

US 2022/0044402 A1  Feb. 10, 2022

Related U.S. Application Data

(60) Provisional application No. 63/062,390, filed on Aug. 6, 2020.

(51) Int. Cl.
*G06T 7/00* (2017.01)
*A61B 6/00* (2024.01)
*A61B 6/03* (2006.01)
*A61B 6/50* (2024.01)
*G06T 7/11* (2017.01)
*G16H 15/00* (2018.01)
(Continued)

(52) U.S. Cl.
CPC ............ *G06T 7/0012* (2013.01); *A61B 6/032* (2013.01); *A61B 6/50* (2013.01); *A61B 6/5217* (2013.01); *G06T 7/11* (2017.01); *G16H 15/00* (2018.01); *G16H 30/20* (2018.01); *G16H 30/40* (2018.01); *G16H 50/20* (2018.01); *G16H 50/30* (2018.01); *G06T 2207/10081* (2013.01); *G06T 2207/30061* (2013.01); *G16H 20/40* (2018.01)

(58) Field of Classification Search
CPC ...................... G06T 7/0012; G06T 7/11; G06T 2207/10081; G06T 2207/30061; A61B 6/032; A61B 6/50; A61B 6/5217; G16H 15/00; G16H 30/20; G16H 30/40; G16H 50/20; G16H 50/30; G16H 20/40
See application file for complete search history.

(56) References Cited

U.S. PATENT DOCUMENTS 7,798,147 B2   9/2010   Hendricksen et al.
7,819,908 B2   10/2010  Ingenito
(Continued)

OTHER PUBLICATIONS

Klinder et al., Lobar fissure detection using line enhancing filters, Proc. SPIE 8669, Medical Imaging 2013: Image Processing, 86693C, Mar. 13, 2013.
(Continued)

*Primary Examiner* — Colin T. Sakamoto
*Assistant Examiner* — Andrew W Begeman
(74) *Attorney, Agent, or Firm* — Kilpatrick Townsend & Stockton LLP

(57) ABSTRACT

Devices, methods, and systems are provided for analyzing lung imaging data. Lung imaging data may be analyzed to segment the lung, identify fissure locations, calculate fissure defect scores, identify adjacent lung compartments, calculate emphysema scores, calculate volumes, and calculate proximities. Collateral ventilation within a lung compartment may be determined based on the analyzed lung imaging data.

19 Claims, 5 Drawing Sheets

(51) Int. Cl.
*G16H 30/20* (2018.01)
*G16H 30/40* (2018.01)
*G16H 50/20* (2018.01)
*G16H 50/30* (2018.01)
*G16H 20/40* (2018.01)

(56) References Cited

U.S. PATENT DOCUMENTS

| | | | |
|---|---|---|---|
| 8,136,526 | B2 | 3/2012 | Perkins et al. |
| 8,137,302 | B2 | 3/2012 | Aljuri et al. |
| 8,445,589 | B2 | 5/2013 | Ingenito et al. |
| 2008/0009760 | A1 | 1/2008 | Wibowo et al. |
| 2008/0086107 | A1* | 4/2008 | Roschak ........... A61M 25/0068 604/506 |
| 2011/0087122 | A1* | 4/2011 | Aljuri .................... A61B 5/08 128/200.24 |
| 2015/0238270 | A1* | 8/2015 | Raffy ................... A61B 90/37 600/407 |
| 2015/0294462 | A1 | 10/2015 | Yin et al. |
| 2016/0328850 | A1* | 11/2016 | Yin ......................... G16H 50/80 |
| 2017/0224301 | A1* | 8/2017 | Radhakrishnan ........ A61B 6/50 |

OTHER PUBLICATIONS

Kuhnigk, Jan-Martin, et al., Informatics in radiology (infoRAD): New Tools for Computer Assistance in thoracic CT. Part 1. Functional Analysis of Lungs, Lung Lobes, and Broncho pulmonary Segments, Radiographics. Mar.-Apr. 2005; vol. 25 No. 2; pp. 525-536.

Lassen et al., Automatic segmentation of lung lobes in CT images based on fissures, vessels, and bronchi, in IEEE Transactions on Medical Imaging, vol. 32, No. 2, pp. 210-222, Feb. 2013.

Lassen et al., Interactive lung lobe segmentation and correction in tomographic images, Proc. SPIE 7963, Medical Imaging 2011: Computer-Aided Diagnosis, 79631S (Mar. 8, 2011).

Lassen et al., Lung and lung lobe segmentation methods at Fraunhofer MEVIS, 2011, Lobe and Lung Analysis (LOLA11) Challenge; pp. 185-199.

PCT/US2021/044406 International Search Report and Written Opinion of the International Searching Authority dated Nov. 22, 2021.

Qian et al., Elastic contour model-based analysis of structural deformations: toward time-sequenced regional lung parenchymal analysis, Proc. SPIE 2709, Medical Imaging 1996: Physiology and Function from Multidimensional Images, (Apr. 8, 1996).

Reinhardt et al., 3D pulmonary CT image registration with a standard lung atlas, Proc. SPIE 3978, Medical Imaging 2000: Physiology and Function from Multidimensional Images, (Apr. 20, 2000).

Reinhardt et al., Detection of lung lobar fissures using fuzzy logic, Proc. SPIE 3660, Medical Imaging 1999: Physiology and Function from Multidimensional Images, (May 20, 1999).

Kuhnigk, et al., Lung lobe segmentation by anatomy-guided 3D watershed transform. Medical Imaging 2003: Image Processing, vol. 4, No. 23. Editors: Milan Sonka, Univ. of Iowa; J. Michael Fitzpatrick, Vanderbilt Univ., Proc. of SPIE vol. 5032 (May 15, 2003), pp. 1482-1490.

Reinhardt, Joseph M., et al. Pulmonary imaging and analysis. Handbook of medical imaging, vol. 2, Medical Image Processing and Analysis; Editors: J. Michael Fitzpatrick; Milan Sonka; published Jun. 14, 2000; pp. 1005-1060.

Revel et al, Automated lobar quantification of emphysema in patients with severe COPD, European Radiology, Dec. 2008, vol. 18, No. 12; pp. 2723-2730.

Schmidt-Richberg et al., Evaluation of Algorithms for Lung Fissure Segmentation in CT Images. In: Tolxdorff T., Deserno T., Handels H., Meinzer HP. (eds) Bildverarbeitung für die Medizin 2012. Informatik aktuell. Springer, Berlin, Heidelberg (First Online: Mar. 16, 2012).

Sluimer et al., Toward automated segmentation of the pathological lung in CT, IEEE Trans Med Imaging. Aug. 2005; vol. 24 No. 8, pp. 1025-1038.

Wiemker et al., Unsupervised extraction of the pulmonary interlobar fissures from high resolution thoracic CT data, International Congress Series, vol. 1281, May 2005; pp. 1121-1126.

Xiao et al., Pulmonary Fissure Detection in CT Images Using a Derivative of Stick Filter, IEEE Transactions on Medical Imaging, vol. 35, No. 6, Jun. 2016.

Zhang et al., Atlas-Driven Lung Lobe Segmentation in Volumetric X-Ray CT Images, IEEE Transactions on Medical Imaging, vol. 25, No. 1, Jan. 2006.

Zhang et al, Lung lobe segmentation by graph search with 3D shape constraints, Proc. SPIE 4321, Medical Imaging 2001: Physiology and Function from Multidimensional Images, (May 21, 2001).

* cited by examiner

METHODS, SYSTEMS, AND DEVICES FOR ANALYZING LUNG IMAGING DATA TO DETERMINE COLLATERAL VENTILATION

CROSS-REFERENCE TO RELATED APPLICATIONS

This application claims the benefit of U.S. Provisional No. 63/062,390, filed Aug. 6, 2020, the entire content of which is incorporated herein by reference.

FIELD OF THE INVENTION

The present disclosure relates generally to devices, methods, and systems for analyzing lung imaging data.

BACKGROUND

Pulmonary diseases, such as chronic obstructive pulmonary disease, (COPD), reduce the ability of one or both lungs to fully expel air during the exhalation phase of the breathing cycle. Such diseases are accompanied by chronic or recurrent obstruction to air flow within the lung. Because of the increase in environmental pollutants, cigarette smoking, and other noxious exposures, the incidence of COPD has increased dramatically in the last few decades and now ranks as a major cause of activity-restricting or bed-confining disability in the United States. COPD can include such disorders as chronic bronchitis, bronchiectasis, asthma, and emphysema.

It is known that emphysema and other pulmonary diseases reduce the ability of one or both lungs to fully expel air during the exhalation phase of the breathing cycle. One of the effects of such diseases is that the diseased lung tissue is less elastic than healthy lung tissue, which is one factor that prevents full exhalation of air. During breathing, the diseased portion of the lung does not fully recoil due to the diseased (e.g., emphysematic) lung tissue being less elastic than healthy tissue. Consequently, the diseased lung tissue exerts a relatively low driving force, which results in the diseased lung expelling less air volume than a healthy lung. The reduced air volume exerts less force on the airway, which allows the airway to close before all air has been expelled, another factor that prevents full exhalation.

The problem is further compounded by the diseased, less elastic tissue that surrounds the very narrow airways that lead to the alveoli, which are the air sacs where oxygen-carbon dioxide exchange occurs. The diseased tissue has less tone than healthy tissue and is typically unable to maintain the narrow airways open until the end of the exhalation cycle. This traps air in the lungs and exacerbates the already-inefficient breathing cycle. The trapped air causes the tissue to become hyper-expanded and no longer able to effect efficient oxygen-carbon dioxide exchange.

In addition, hyper-expanded, diseased lung tissue occupies more of the pleural space than healthy lung tissue. In most cases, a portion of the lung is diseased while the remaining part is relatively healthy and, therefore, still able to efficiently carry out oxygen exchange. By taking up more of the pleural space, the hyper-expanded lung tissue reduces the amount of space available to accommodate the healthy, functioning lung tissue. As a result, the hyper-expanded lung tissue causes inefficient breathing due to its own reduced functionality and because it adversely affects the functionality of adjacent healthy tissue.

Some recent treatments include the use of devices that isolate a diseased region of the lung in order to reduce the volume of the diseased region, such as by collapsing the diseased lung region. According to such treatments, a delivery catheter is used to implant one or more implantable devices in airways feeding a diseased region of the lung to regulate fluid flow to the diseased lung region in order to fluidly isolate the region of the lung. These implantable devices can be, for example, one-way valves that allow flow in the exhalation direction only, occluders or plugs that prevent flow in either direction, or two-way valves that control flow in both directions.

It has been suggested that the use of endobronchial implants for lung volume reduction might be most effective when applied to lung compartments which are not affected by collateral ventilation. Collateral ventilation occurs when air passes from one lung compartment to another through a collateral channel rather than the primary airway channels. If collateral airflow channels are present in a lung compartment, implanting a one-way valve or occluder might not be as effective, because the compartment might continue to fill with air from the collateral source and thus fail to collapse as intended. In many cases, COPD manifests itself in the formation of a large number of collateral channels caused by rupture of alveoli due to hyperinflation, or by destruction and weakening of alveolar tissue.

In addition to the above, it is sometimes desirable to provide methods for sealing collateral flow channels between adjacent lung segments. Such sealing methods may be particularly useful for treating patients prior to endobronchial or other lung volume reduction procedures. Thus, methods and apparatus for sealing collateral flow channels should be compatible with known protocols for occluding diseased lung segments and regions for performing lung volume reduction, including the placement of plugs and occluding members within the airways leading to such diseased lung segments and regions. In other cases, sealing agents may be provided, though they are not equipped with the systems or methods for delivery for collateral channels.

Imaging techniques such as X-ray computed tomography (CT) may be used in assessment of disease and treatment planning. Disease and anatomical features of a lung may be difficult to determine through visual inspection of CT images. It is thus desirable to provide methods, systems, and devices for analyzing imaging data. At least some of these objectives will be met by the inventions described herein below.

SUMMARY

The present disclosure relates to aspects of methods, devices, and systems for analyzing lung imaging data. In one aspect, a method of assessing collateral ventilation in a lung of a patient comprises analyzing computerized tomography data of a lung. Analyzing computerized tomography data of a lung may comprise segmenting the lung into separate lung compartments, calculating an emphysema score for one or more regions of one or more lung compartments based on a density mask, identifying a fissure defect, calculating a fissure defect score based on a size of the fissure defect, determining a proximity of the fissure defect to the region of the lung compartment, and determining whether collateral ventilation is present or above a threshold level in the lung compartment based on the calculated emphysema score, fissure defect score, and the proximity of the fissure defect to the region of the lung compartment. In an embodiment, collateral ventilation may be determined to be present or above a threshold level if the region of the lung compartment has an emphysema score above a threshold emphysema score value, that the fissure defect has a fissure defect score above a threshold fissure defect score value, and that the proximity of the fissure defect to the region of the lung compartment is within a threshold proximity. Methods may further comprise calculating a collateral ventilation score for the lung compartment based on the emphysema score, fissure defect score, and proximity of the fissure defect to the region of the lung compartment. Collateral ventilation may be determined to be present or above a threshold level in the lung compartment based on the calculated collateral ventilation score. Methods may also comprise determining a degree of collateral ventilation based on the calculated collateral ventilation score. Collateral ventilation may be determined to be present or above a threshold level in the lung compartment based on which fissure comprises the fissure defect, where on the fissure the fissure defect is located, or which lung compartments the fissure defect separates. The method may further comprise identifying airways. Determining whether collateral ventilation is present or above a threshold level in the lung compartment may be based on whether an airway is identified within a threshold proximity to the region of the lung compartment. Determining whether collateral ventilation is present or above a threshold level in the lung compartment may be based on whether an airway is identified within a threshold proximity to the fissure defect.

In an embodiment, analyzing computerized tomography data of a lung comprises segmenting the lung into separate lung compartments; identifying a fissure defect; identifying lung compartments adjacent to the fissure defect; calculating emphysema scores for one or more regions of a first lung compartment adjacent to the fissure defect and for one or more regions of a second lung compartment adjacent to the fissure defect on an opposing side of the fissure defect based on a density mask; calculating a fissure defect score based on a size of the fissure defect; determining proximities of the fissure defect to the region of the first lung compartment and the region of the second lung compartment; and determining whether collateral ventilation is present or above a threshold level in the first or second lung compartment based on the calculated emphysema score, fissure defect score, and the proximities of the fissure defect to the region of the first and second lung compartments. Collateral ventilation may be determined to be present or above a threshold level if the region of the first lung compartment has an emphysema score above a threshold emphysema score value, the region of the second lung compartment has an emphysema score above a threshold emphysema score value, the fissure defect has a fissure defect score above a threshold fissure defect score value, the proximity of the fissure defect to the region of the first lung compartment is within a threshold proximity, and the proximity of the fissure defect to the region of the second lung compartment is within a threshold proximity. Methods may further comprise calculating a collateral ventilation score for the first or second lung compartment based on the emphysema scores of the regions of the first and second lung compartments, fissure defect score, and proximities of the fissure defect to the regions of the first and second lung compartments. Collateral ventilation may be determined to be present or above a threshold level in the lung compartment based on the calculated collateral ventilation score. Methods may also comprise determining a degree of collateral ventilation based on the calculated collateral ventilation score.

In another aspect, a method of assessing collateral ventilation in a lung of a patient comprises analyzing computerized tomography data of a lung. Analyzing computerized tomography data of a lung may comprise segmenting the lung into separate lung compartments, identifying a fissure defect, identifying lung compartments adjacent to the fissure defect, determining changes in volumes of a target lung compartments adjacent to the fissure defect and another lung compartment sharing a boundary with the fissure defect during breathing, and determining whether collateral ventilation is present or if a degree of collateral ventilation is above a threshold level in a target lung compartment based on the changes in volumes of the target lung compartment and the other lung compartment sharing a boundary with the fissure defect. Methods may further comprise calculating a fissure defect score based on a size of the fissure defect. Determining whether collateral ventilation is present is may be further based on the calculated defect score. Methods may further comprise determining a degree of collateral ventilation based on the changes in volume of the target lung compartment and the other lung compartment sharing a boundary with the fissure defect and on the size of the fissure defect.

Various methods may comprise creating a report indicating lung compartments determined to have collateral ventilation or degrees of collateral ventilation for lung compartments. The report may comprise potential treatment sites and suggested implantable devices for the potential treatment sites to cause lung volume reduction or reduce hyperinflation, wherein the potential treatment sites are airways leading to lung compartments determined not to have collateral ventilation or a degree of collateral ventilation below a threshold level. Additionally or alternatively, the report may comprise one or more potential treatment sites and one or more suggested therapeutic agents or implantable devices to be delivered to the potential treatment sites to cause lung volume reduction or reduce hyperinflation, wherein the potential treatment sites comprise one or more regions within lung compartments determined to have collateral ventilation or a degree of collateral ventilation above a threshold level. The report may comprise one or more potential treatment sites and one or more suggested therapeutic agents or implantable devices to be delivered to minimize collateral ventilation between lung compartments, wherein the potential treatment sites comprise one or more airways leading to a fissure defect adjacent to lung compartments determined to have collateral ventilation or a degree of collateral ventilation above a threshold level.

This and other aspects of the present disclosure are described herein.

BRIEF DESCRIPTION OF THE DRAWINGS

Present embodiments have other advantages and features which will be more readily apparent from the following detailed description and the appended claims, when taken in conjunction with the accompanying drawings, in which:

DETAILED DESCRIPTION

Figure 1:
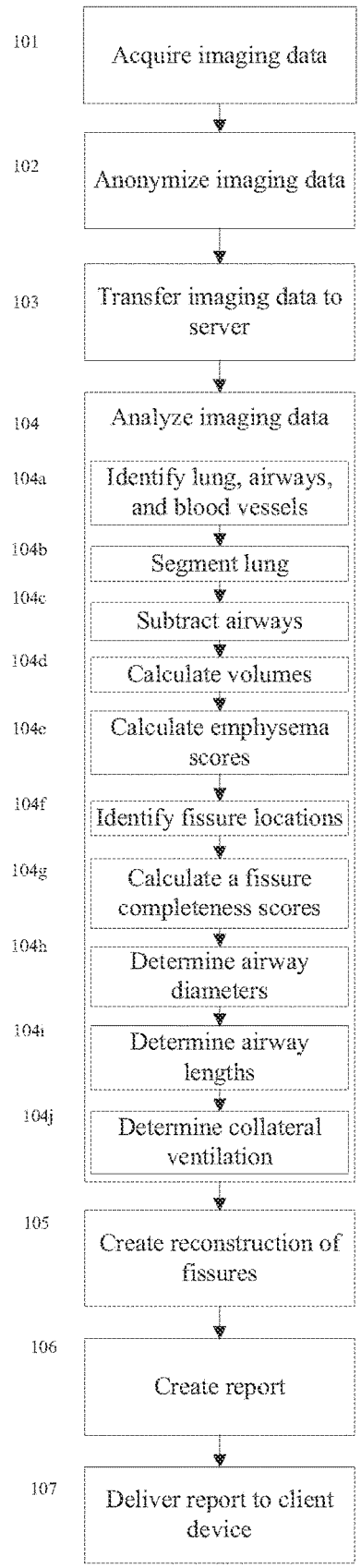
FIG. 1 shows a method for analyzing imaging data of a lung.

While the invention has been disclosed with reference to certain embodiments, it will be understood by those skilled in the art that various changes may be made and equivalents may be substituted without departing from the scope of the invention. In addition, many modifications may be made to adapt to a particular situation or material to the teachings of the invention without departing from its scope.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

The word "exemplary" is used herein to mean "serving as an example, instance, or illustration." Any implementation described herein as "exemplary" is not necessarily to be construed as advantageous over other implementations.

The present application provides methods and systems for targeting, accessing and diagnosing diseased lung compartments. Such compartments could be an entire lobe, a segment, a sub-segment or any such portion of the lung. Diagnosis is achieved in the disclosed embodiments by isolating a lung compartment to obtain various measurements to determine lung functionality. Though COPD is mentioned as an example, the applicability of these methods for treatment and diagnosis is not limited to COPD, but can be applicable to any lung disease.

The present disclosure describes methods, systems, and devices for analyzing CT data of a lung. While analysis of X-ray computed tomography (CT) data is described throughout, it is contemplated that other imaging data such as magnetic resonance imaging (MM) data, 3D ultrasound data, positron emission tomography (PET) data, single-photon emission computed tomography (SPECT) data, etc. may be used additionally or alternatively.

Figure 2:
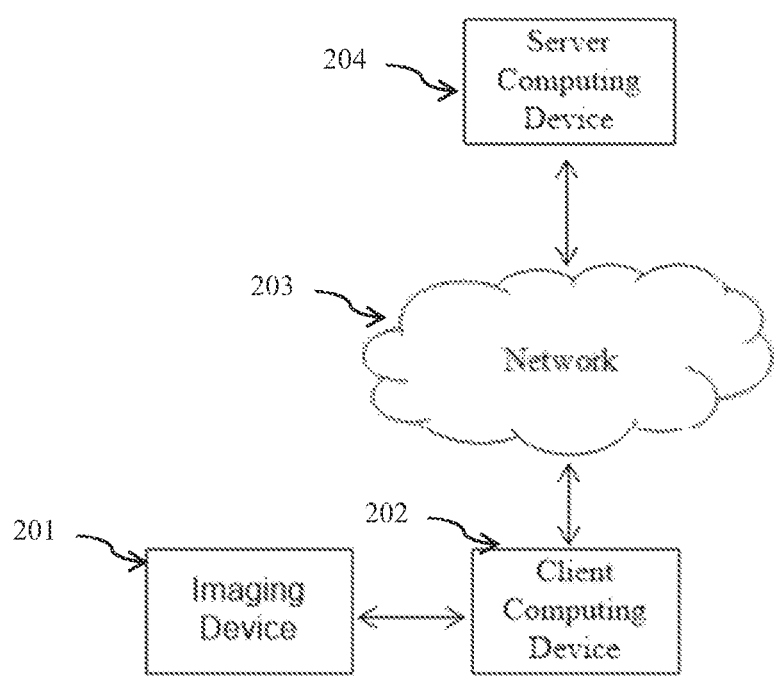
FIG. 2 shows an exemplary system architecture.

FIG. 1 shows a method for analyzing CT data of a lung. A corresponding exemplary system architecture is shown in FIG. 2. The method may include some or all of the steps in FIG. 4 or 5. At step 101 a client device 202 acquires CT data of a lung from an imaging device 201. CT data may comprise static CT image data, dynamic CT image data during one or more breathing cycles, and/or data from multiple static CT images at different points during one or more the breathing cycles. CT data may be collected during inspiration and/or expiration. CT data may be of various formats such as Digital Imaging and Communications in Medicine (DICOM). At step 102 patient identifiable data is removed from the CT data on the client computing device 202 in order to anonymize the CT data. At step 103 anonymized CT data is transferred over network 203 to a server computing device 204.

At step 104 server computing device 204 analyzes the CT data. Methods for analyzing CT imaging data have been described in Kuhnigk, Jan-Martin, et al. "Informatics in radiology (infoRAD): new tools for computer assistance in thoracic CT. Part 1. Functional analysis of lungs, lung lobes, and bronchopulmonary segments." *Radiographics: a review publication of the Radiological Society of North America, Inc* 25.2 (2004): 525-536., Kuhnigk, Jan-Martin, et al. "Lung lobe segmentation by anatomy-guided 3D watershed transform." *Medical Imaging* 2003. International Society for Optics and Photonics, 2003, Zhang, Li, and Joseph M. Reinhardt. "Detection of lung lobar fissures using fuzzy logic." *Medical Imaging* '99. International Society for Optics and Photonics, 1999, Zhang, Li, and Joseph M. Reinhardt. "3D pulmonary CT image registration with a standard lung atlas." *Medical Imaging* 2000. International Society for Optics and Photonics, 2000, Qian, Jiang, Theophano Mitsa, and Eric A. Hoffman. "Elastic contour model-based analysis of structural deformations: toward time-sequenced regional lung parenchymal analysis." *Medical Imaging* 1996. International Society for Optics and Photonics, 1996, Reinhardt, Joseph M., et al. "Pulmonary imaging and analysis." *Handbook of medical imaging* 2 (2000): 1005-1060, Zhang, Li, Eric A. Hoffman, and Joseph M. Reinhardt. "Atlas-driven lung lobe segmentation in volumetric X-ray CT images." *Medical Imaging* 2003. International Society for Optics and Photonics, 2003, Zhang, Li, Eric A. Hoffman, and Joseph M. Reinhardt. "Lung lobe segmentation by graph search with 3D shape constraints." *Medical Imaging* 2001. International Society for Optics and Photonics, 2001, Marie-Pierre Revel, et al, Automated lobar quantification of emphysema in patients with severe COPD, European Radiology December 2008, Volume 18, Issue 12, pp 2723-2730, Wiemker, Rafael, Thomas Billow, and Thomas Blaffert. "Unsupervised extraction of the pulmonary interlobar fissures from high resolution thoracic CT data." *International Congress Series*. Vol. 1281. Elsevier, 2005, Xiao, C., et al. "Pulmonary Fissure Detection in CT Images Using a Derivative of Stick Filter." *IEEE transactions on medical imaging* (2016), Schmidt-Richberg, Alexander, et al. "Evaluation of Algorithms for Lung Fissure Segmentation in CT Images." Bildverarbeitung für die Medizin 2012. Springer Berlin Heidelberg, 2012. 201-206, Klinder, Tobias, Hannes Wendland, and Rafael Wiemker. "Lobar fissure detection using line enhancing filters." SPIE Medical Imaging. International Society for Optics and Photonics, 2013, Lassen, Bianca, et al. "Lung and lung lobe segmentation methods at Fraunhofer MEVIS." *4th Int. MICCAI Workshop Pulmonary Image Anal.*, Toronto, Canada. 2011, Lassen, Bianca, et al. "Automatic segmentation of lung lobes in CT images based on fissures, vessels, and bronchi." Biomedical Imaging: From Nano to Macro, 2010 IEEE International Symposium on. IEEE, 2010, Lassen, Bianca, et al. "Interactive lung lobe segmentation and correction in tomographic images." *SPIE Medical Imaging*. International Society for Optics and Photonics, 2011, Revel, Marie-Pierre, et al. "Automated lobar quantification of emphysema in patients with severe COPD." *European radiology* 18.12 (2008): 2723-2730, Sluimer, Ingrid, Mathias Prokop, and Bram Van Ginneken. "Toward automated segmentation of the pathological lung in CT." *Medical Imaging, IEEE Transactions on* 24.8 (2005): 1025-1038.c, the full disclosures of which are hereby incorporated by reference.

Optionally, quality control checks may be performed to ensure scans are of adequate quality for processing. Analysis of the CT data may comprise some or all of steps 104a-104j. Some or all of steps 104a-104j may be performed sequentially in various orders. Additionally or alternatively, some or all of steps 104a-104j may be performed in parallel. At step 104a server computing device 204 identifies the lung, airways, and blood vessels using the CT data.

At step 104b server computing device 204 segments the lung. In an embodiment the lung is segmented into five separate lobes, the right upper lobe, the right middle lobe, the right lower lobe, the left upper lobe, and the left upper lobe. Each lobe may be further segmented into separate lung segments. Lung segments may also be further segmented into separate lung sub-segments.

At step 104c server computing device 204 subtracts the airways. In an embodiment, airways are subtracted until the third generation. In other embodiments, more or less generations of airways may be subtracted.

At step 104d server computing device 204 calculates volumes of the lobes. In an embodiment, volumes of separate lung segments may be calculated. Server computing device 204 may also calculate volumes of separate lung sub-segments. Volumes of lobes, lung segments, and/or lung sub-segments may be determined throughout one or more breathing cycles and change in volume may be determined. Volume and/or change in volume of a lung compartment may be compared to volume or change in volume of another lung compartment.

At step 104e server computing device 204 calculates emphysema scores for the lobes. Emphysema scores may be calculated using density masks at various user defined thresholds, for example, −910 Hounsfield or −950 Hounsfield units. In an embodiment, emphysema scores for separate lung segments may be calculated. Server computing device 204 may also calculate emphysema scores for separate lung sub-segments. Emphysema scores may also be calculated for regions within lobes, lung segments, and/or lung sub-segments.

At step 104f server computing device 204 identifies fissure locations. At step 104g server computing device 204 identifies fissure completeness for each fissure or portions of each fissure. The system may be configured to identify fissure defects and locations of fissure defects. The system may also be configured to determine sizes and/or severity of fissure defects and calculate fissure defect scores. Fissure defect sizes or severities may be determined as a dimension of the defect or as a percentage of the fissure or portion of the fissure comprising the fissure defect. Fissure completeness scores may be calculated for each lobe. Fissure completeness scores may represent the percentage complete of the portions of the fissures touching each lobe. For example, the fissure completeness score of the right upper lobe may be based on the completeness of the horizontal fissure and the completeness of the portion of the right oblique fissure that separates the right upper lobe from the right lower lobe. Similarly, the fissure completeness score of the right middle lobe may be based on the completeness of the horizontal fissure and the completeness of the portion of the right oblique fissure that separates the right middle lobe from the right lower lobe. Fissure completeness scores may also be calculated for separate lung segments and/or separate lung sub-segments. The system may identify which lobes, segments, and sub-segments are in contact with one of the locations where a fissure is incomplete. Proximity of lobes, segments, sub-segments, or regions within a lung compartment and locations where a fissure is incomplete may be determined.

At step 104h server computing device 204 may determine airway diameters. In an embodiment, diameters for lobar bronchi, segmental bronchi, and sub-segmental bronchi are determined for each lobe. At step 104i server computing device 204 may determine airway lengths. In an embodiment distances from an ostium to a distal carina may be determined for lobar bronchi, segmental bronchi, and sub-segmental bronchi.

Figure 4:
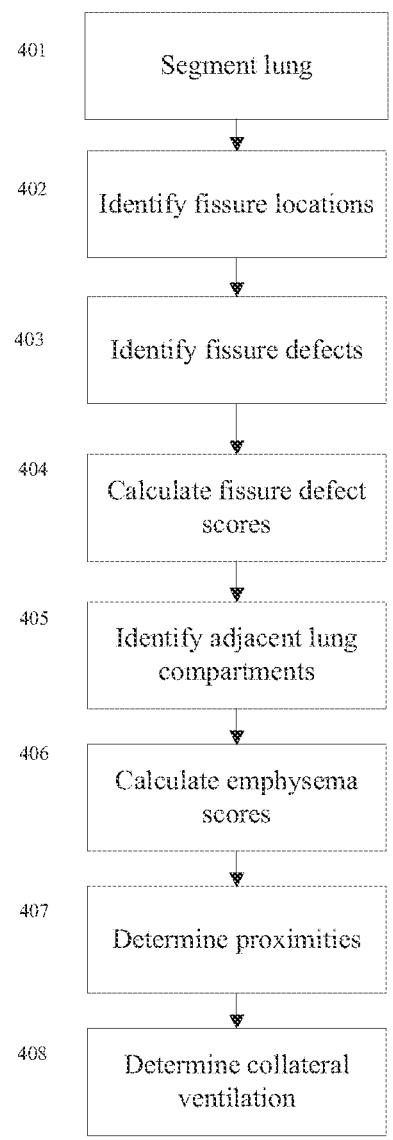
FIG. 4 shows one embodiment of a method for analyzing imaging data of a lung to determine collateral ventilation.
Figure 5:
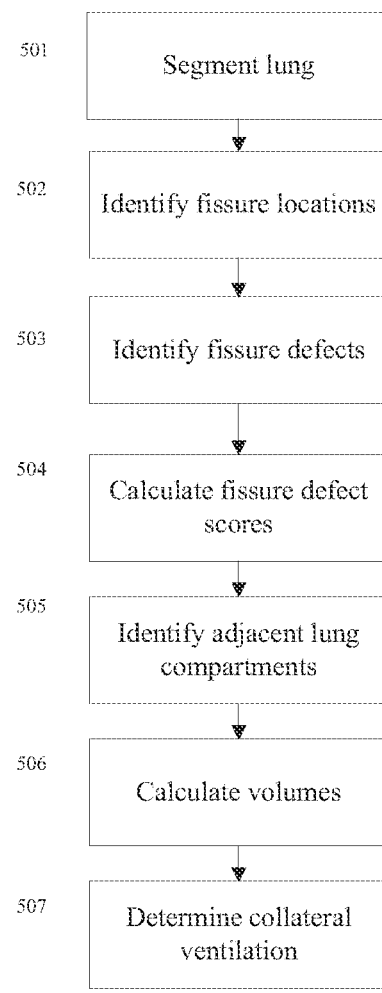
FIG. 5 shows another embodiment of a method for analyzing imaging data of a lung to determine collateral ventilation.

At step 104j server computing device 204 may determine the presence or absence of collateral ventilation, whether collateral ventilation is above or below a threshold level, or a degree of collateral ventilation for a lobe, lung segment, and/or lung sub-segment. Collateral ventilation and degree of collateral ventilation may be determined based on data derived from any of the steps in 104a-104i. Embodiments of methods for determining collateral ventilation are shown in FIGS. 4 and 5. In an embodiment, collateral ventilation and degree of collateral ventilation may be determined based on the emphysema scores of a lobe, lung segment, lung sub-segment, or regions of a lung sub-segment calculated in step 104e. Collateral ventilation and degree of collateral ventilation may also be determined based on the fissure data determined in steps 104f and 104g. Fissure defect locations, fissure defect scores, and fissure completeness scores of a fissure or portion of a fissure adjacent to or near a lobe, lung segment, lung sub-segment, or region of a lung sub-segment may be used to determine the presence of collateral ventilation or a degree of collateral ventilation. Collateral ventilation and degree of collateral ventilation may also be determined based on the volumes or changes in volumes of one or more lung compartments determined in step 104d.

At step 105 server computing device 204 creates a three-dimensional reconstruction of the fissures indicating locations where the fissures are incomplete. In an embodiment, the reconstruction of the fissures may be color coded or comprise a heat map to indicate completeness. At step 106 server computing device 204 creates a report comprising fissure scores, volumes, and emphysema scores for each lobe. The report may be exportable in various electronically viewable or printable formats such as Portable Document Format (PDF), word processing documents, images such as JPEG, videos, etc. In an embodiment, the report comprises fissure scores, volumes, and emphysema scores for separate lung segments. The report may also comprise fissure scores, volumes, and emphysema scores for separate lung sub-segments. The report may also comprise the three-dimensional reconstruction of the fissures.

Figure 3:
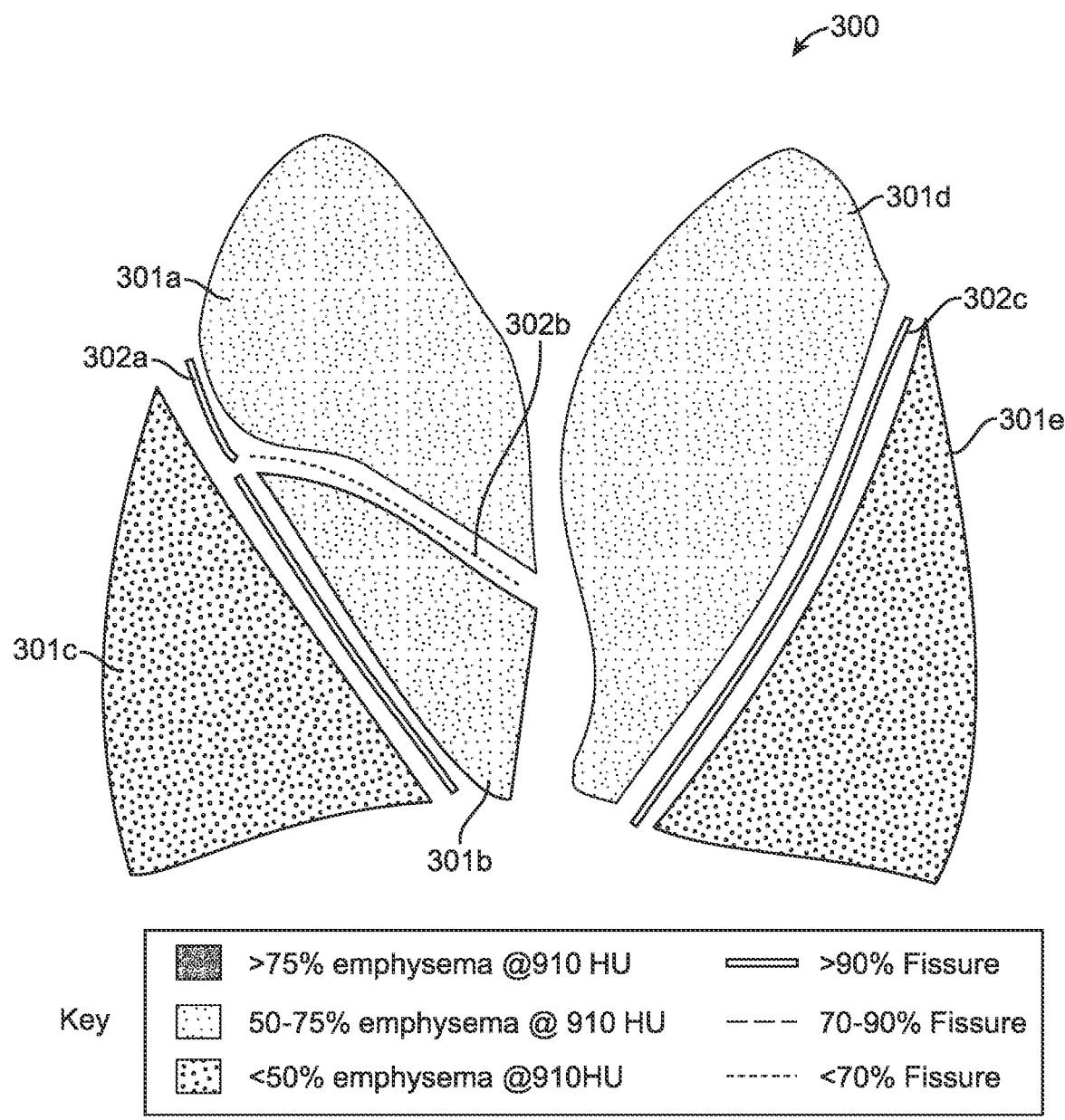
FIG. 3 shows an exemplary graphical representation of a lung indicating emphysema score and fissure completeness.

FIG. 3 shows an exemplary graphical representation of a lung included in the report. The report may comprise a two-dimensional graphical representation of the lung 300 with the five lobes 301a-301e identified. The lobes 301a-301e are shaded or colored in the two-dimensional graphical representation to indicate the emphysema score. Fissures 302a-302c may be identified in the two-dimensional graphical representation with lines that indicate completeness of the fissure 302a-302c. Fissure lines may have varying shading, color coding, thickness, or solid versus dashed lines to indicate completeness of the fissure 302a-302c. Fissures 302a-302c may be classified into different categories with different line types based on the completeness of the fissure 302a-302c for that location. In an embodiment, fissures 302a-302c receive a first type of line if they have high completeness with a fissure score greater than a specified fissure percent complete (e.g., >95%), a second type of line if they have low completeness with a fissure score less than specified fissure percent complete (e.g., <80%), or a third type of line if they have intermediate completeness with a fissure score specified percent complete defined as between high and low completeness scores (e.g., between 80% to 95%).

The report may indicate locations of fissure defects and size or severity of fissure defects. The report may indicate lung compartments identified to be in contact with a location where a fissure is incomplete. In an embodiment, the report indicates calculated emphysema scores for lobes, lung segments, lung sub-segments, or regions within lobes, lung segments, or lung sub-segments. The report may also indicate proximities of fissure defects to lung compartments, regions within lung compartments, or airways. In various embodiments, the report may indicate lobes, lung segments, or lung sub-segments determined to have collateral ventilation or collateral ventilation above a threshold level. The report may indicate degrees of collateral ventilation for lung compartments.

The report may further comprise a three-dimensional graphical representation of the lung with each lobe identified. Lobes may be shaded or colored in the three-dimensional graphical representation to indicate the emphysema score. In an embodiment, the three-dimensional graphical representation of the lung may identify each lung segment and/or each lung sub-segment. Lung segments and/or lung sub-segments may be shaded or colored in the three-dimensional graphical representation to indicate the emphysema score. Fissures may be identified in the three-dimensional graphical representation with lines that indicate completeness of the fissure. In an embodiment, the report contains multiple two-dimensional graphical representations of cross sections of the lung. The three-dimensional model may be provided as a video or interactive model wherein the lung is rotatable to view lung model from multiple viewing angles.

The report may be annotated and customized for the specific lung. Annotation and customization may include patient selection information, personalized treatment planning information, identification of regions of interest, potential treatment sites, and/or suggested treatments.

The report may comprise treatment suggestions for using implantable devices such as endobronchial valves, clips, or plugs to cause lung volume reduction or reduce hyperinflation. In an embodiment, the implantable device is a one-way flow control valve configured to allow air to flow out of the target lung compartment and prevent air flow into the target lung compartment, thus causing volume reduction or collapse of the target lung region. Examples of such implants and methods are described, for example, in U.S. Pat. Nos. 8,136,526 and 7,798,147, the full disclosures of which are hereby incorporated by reference. In an embodiment, the report contains the airway diameters and distances determined in steps 104h and 104i. Server computing device 204 may be configured to compare the determined diameters and distances to known diameters and lengths of implantable devices and create a treatment plan with potential treatment sites based on an ideal combination of devices to be placed. The report may include potential treatment sites and suggested implantable devices having diameters and lengths matching the diameters and distances determined for the potential treatment sites. The potential treatment sites for the implantable devices may be selected as airways leading to lung compartments determined not to have collateral ventilation or degrees of collateral ventilation below a threshold level.

Additionally or alternatively, the report may comprise treatment suggestions for using therapeutic agents such as sealants to cause lung volume reduction, reduce hyperinflation, or minimize collateral ventilation between lung compartments. Examples of such therapeutic agents and methods are described, for example, in U.S. Pat. Nos. 8,137,302, 7,819,908 and 8,445,589, the full disclosures of which are hereby incorporated by reference. The report may include potential treatment sites and suggested therapeutic agents or implantable devices. The potential treatment sites may be one or more regions within lung compartments determined to have collateral ventilation or degrees of collateral ventilation above a threshold level. The potential treatment sites may also be airways leading to fissure defects adjacent to lung compartments determined to have collateral ventilation or degrees of collateral ventilation above a threshold level.

With any of the suggested treatment options, the report may comprise navigation information for accessing potential treatment sites. In an embodiment, the report comprises a three-dimensional airway model. Additionally or alternatively, the report may comprise a two-dimensional image of an entrance to each airway. The report may also provide a video fly-through and/or two dimensional turn-by-turn steps for accessing the region of interest from the trachea.

At step 107 server computing device 204 delivers the report to client device 202 or other computing device over the network. Optionally, user identifiable information removed at step 102 may be added to the report on the client device 202.

FIG. 4 shows one embodiment of a method for determining collateral ventilation of a lung compartment based on fissure defects and emphysema scores. Collateral ventilation may be determined for a lobe, lung segment, or lung sub-segment. The method may include some or all of the steps in FIG. 1 or 5. Some or all of the steps may be performed sequentially in various orders. Additionally or alternatively, some or all of steps may be performed in parallel. Some or all of the steps may be performed at the level of the whole lung, lobe, lung segment, or lung sub-segment. At step 401 the system segments the lung. In an embodiment the lung is segmented into five separate lobes, the right upper lobe, the right middle lobe, the right lower lobe, the left upper lobe, and the left upper lobe. Each lobe may be further segmented into separate lung segments. Lung segments may also be further segmented into separate lung sub-segments.

At step 402 the system identifies fissure locations. At step 403 the system identifies fissure completeness for each fissure or portions of each fissure. The system may be configured to identify fissure defects and locations of fissure defects. At step 404 the system may also be configured to determine sizes and/or severity of fissure defects and calculate fissure defect scores. Fissure defect scores may represent a size or dimension of the defect, a severity of the defect, a percentage of the fissure comprising a fissure defect, and/or a percentage of the portion of the fissure adjacent to or near a lung compartment comprising a fissure defect. Fissure completeness scores may also be calculated for each fissure or portions of fissures adjacent to or nearby lung compartments. At step 405 lung compartments adjacent to or near fissure defects are identified.

At step 406 the system calculates emphysema scores for the lobes, lung segments, lung sub-segments, and/or regions within lobes, lung segments, or lung sub-segments. Emphysema scores may be calculated using density masks at various user defined thresholds, for example, −910 Hounsfield or −950 Hounsfield units.

At step 407 the system determines proximities of fissure defects to adjacent or nearby lung compartments having a high emphysema score or emphysema score above a threshold. Additionally or alternatively, proximity of fissure defects to regions within adjacent or nearby lung compartments may be identified. Proximities of airways to lung compartments, regions within lung compartments, and/or fissure defects may also be determined.

At step 408 the system may determine the presence or absence of collateral ventilation for a lobe, lung segment, and/or lung sub-segment. The system may also determine a level of collateral ventilation for a lobe, lung segment, and/or lung sub-segment. Collateral ventilation and degree of collateral ventilation may be determined based on the calculated emphysema score, fissure defect or completeness score, and the proximity of the fissure defect to the lung compartment or region of the lung compartment. A high emphysema score near a large fissure defect may indicate collateral ventilation.

In various embodiments, collateral ventilation may be determined to be present, likely, significant, or above a threshold level in the lung compartment if the lung compartment (or region within the lung compartment) has an emphysema score above a threshold value, the fissure defect has a fissure defect score above a threshold value (or the fissure completeness score is below a threshold value), and the proximity of the fissure defect to the lung compartment (or region within the lung compartment) is within a threshold proximity. The threshold proximity may be in the range of approximately 0-1 mm, 1-2 mm, 2-5 mm, 5-10 mm, or above 10 mm. In various embodiments, the threshold fissure defect score may be in the range of approximately 0.1-1% defect, 1-2% defect, 2-5% defect, above 5% defect, 1-2 mm defect, 2-5 mm defect, 5-10 mm defect, 10-20 mm defect, or above 20 mm defect. Similarly, collateral ventilation may be determined not to be present, unlikely, insignificant, or below a threshold level if the emphysema score is below a threshold value, the fissure defect score is below a threshold value (or the fissure completeness score is above a threshold value), and/or the proximity is greater than a threshold value.

In some embodiments, a collateral ventilation score for lung compartments may be calculated based on the emphysema score of the lung compartment (or region within the lung compartment), fissure defect score (or fissure completeness score), and the proximity of the fissure defect to the lung compartment (or region within the lung compartment). Collateral ventilation may be determined to be present, likely, or significant in the lung compartment if the collateral ventilation score is above a threshold value. Similarly, collateral ventilation may be determined not to be present, unlikely, or insignificant if the collateral ventilation score is below a threshold value. In an embodiment, a degree of collateral ventilation is determined based on the calculated collateral ventilation score.

Collateral ventilation or degree of collateral ventilation may be determined based on multiple lung compartments adjacent to the same fissure defect. In an embodiment, emphysema scores are calculated for one or more regions of a first lung compartment adjacent to the fissure defect and for one or more regions of a second lung compartment adjacent to the fissure defect on an opposing side of the fissure defect. Proximities of the fissure defect to the regions of both lung may be determined. Collateral ventilation and degree of collateral ventilation may be determined based on the calculated emphysema scores for both lung segments, fissure defect or completeness score, and the proximities of the fissure defect to the lung compartments or regions of the lung compartments. A high emphysema score in both lung compartments near a large fissure defect may indicate collateral ventilation.

Collateral ventilation or degree of collateral ventilation may further determined by which fissure comprises the fissure defect, where on the fissure the fissure defect is located, and/or which lobes, lung segments, or lung sub-segments the fissure defect separates. In an embodiment, the determination of collateral ventilation depends on whether the fissure defect is located on the left oblique fissure separating the left upper lobe from the left lower lobe, the right oblique fissure, the portion of the right oblique fissure that separates the right middle lobe from the right lower lobe, the portion of the right oblique fissure that separates the right upper lobe from the right lower lobe, or the horizontal fissure separating the right upper lobe from the right middle lobe. The determination of collateral ventilation may depend on whether the fissure defect is located on a portion of the fissure separating specific lung segments or lung sub-segments. In additional embodiments, collateral ventilation or degree of collateral ventilation may be further determined based on lung compartment volumes.

The system may be configured to identify airways. Collateral ventilation or degree of collateral ventilation may be determined based on whether an airway is determined to be in communication with or within a threshold proximity to a fissure defect. Collateral ventilation or degree of collateral ventilation may be determined based on whether an airway is identified within a threshold proximity to the region of the lung compartment. In an embodiment, collateral ventilation is determined to be more likely, more significant, or at a higher level if an airway is not identified near the region determined to have a high emphysema score.

FIG. 5 shows an embodiment of a method for determining collateral ventilation a lung compartment based on fissure defects and lung compartment volumes. Collateral ventilation may be determined for a lobe, lung segment, or lung sub-segment. The method may include some or all of the steps in FIG. 1 or 4. Some or all of the steps may be performed sequentially in various orders. Additionally or alternatively, some or all of steps may be performed in parallel. Some or all of the steps may be performed at the level of the whole lung, lobe, lung segment, or lung sub-segment. At step 501 the system segments the lung. In an embodiment the lung is segmented into five separate lobes, the right upper lobe, the right middle lobe, the right lower lobe, the left upper lobe, and the left upper lobe. Each lobe may be further segmented into separate lung segments. Lung segments may also be further segmented into separate lung sub-segments.

At step 502 the system identifies fissure locations. At step 503 the system identifies fissure completeness for each fissure or portions of each fissure. The system may be configured to identify fissure defects and locations of fissure defects. At step 504 the system may also be configured to determine sizes and/or severity of fissure defects and calculate fissure defect scores. Fissure defect scores may represent a size or dimension of the defect, a severity of the defect, a percentage of the fissure comprising a fissure defect, and/or a percentage of the portion of the fissure adjacent to or near a lung compartment comprising a fissure defect. Fissure completeness scores may also be calculated for each fissure or portions of fissures adjacent to or nearby lung compartments. At step 505 lung compartments adjacent to or near fissure defects are identified.

At step 506 the system calculates volumes of lobes, lung segments, and/or lung sub-segments. Volumes of lobes, lung segments, and/or lung sub-segments may be determined throughout one or more breathing cycles and change in volume may be determined. Volumes may be determined by analyzing dynamic CT image data during one or more breathing cycles, and/or data from multiple static CT images at different points during one or more the breathing cycles. CT data may be collected during inspiration and/or expiration.

At step 507 the system may determine the presence or absence of collateral ventilation for a lobe, lung segment, and/or lung sub-segment by evaluating changes in local lung volume around a fissure defect. The system may also determine a level of collateral ventilation for a lobe, lung segment, and/or lung sub-segment. Collateral ventilation and degree of collateral ventilation of a lung compartment may be determined based on the calculated volumes of the lung compartment and another lung compartment adjacent to the fissure defect on an opposing side of the fissure defect. Changes in volume of a lung compartment may be compared to changes in volume of another lung compartment adjacent to the fissure defect on an opposing side of the fissure defect during breathing to identify flow or degree of flow between the lung compartments. In an embodiment, collateral ventilation is determined to be present, likely, significant, or above a threshold level if the target lung compartment and the other lung compartment sharing a boundary with the fissure defect inflate or deflate asynchronously during breathing. In an embodiment, the presence of collateral ventilation or degree of collateral ventilation may further be determined based on the size or severity of the fissure defect.

Collateral ventilation or degree of collateral ventilation may further determined by which fissure comprises the fissure defect, where on the fissure the fissure defect is located, and/or which lobes, lung segments, or lung sub-segments the fissure defect separates. In an embodiment, the determination of collateral ventilation depends on whether the fissure defect is located on the left oblique fissure separating the left upper lobe from the left lower lobe, the right oblique fissure, the portion of the right oblique fissure that separates the right middle lobe from the right lower lobe, the portion of the right oblique fissure that separates the right upper lobe from the right lower lobe, or the horizontal fissure separating the right upper lobe from the right middle lobe. The determination of collateral ventilation may depend on whether the fissure defect is located on a portion of the fissure separating specific lung segments or lung sub-segments. In additional embodiments, collateral ventilation or degree of collateral ventilation may be further determined based on emphysema scores.

Optionally the steps in FIGS. 1, 4, and 5 may be repeated after treatment. Results may be used to compare the lung before and after treatment in order to determine treatment success. In an embodiment, the determined treatment success may be used as feedback to improve future patient selection, identification of regions of interest, and/or determination of treatment options through machine learning.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the invention may also relate to an apparatus or system for performing the operations herein. This apparatus or system may be specially constructed for the required purposes, and/or it may comprise a general-purpose computing device selectively activated or reconfigured by a computer program stored in a computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Imaging device 201, client computing device 202, and server computing device 204 shown in FIG. 2 may comprise various components including but not limited to one or more processing units, memory units, video or display interfaces, network interfaces, input/output interfaces and buses that connect the various units and interfaces. The network interfaces enable the imaging device 201, client computing device 202, and/or server computing device 204 to connect to the network 203. The memory units may comprise random access memory (RAM), read only memory (ROM), electronic erasable programmable read-only memory (EEPROM), and basic input/output system (BIOS). The memory unit may further comprise other storage units such as non-volatile storage including magnetic disk drives, optical drives, flash memory and the like.

While FIG. 2 depicts one imaging device 201, one client computing device 202, one network 203, and one server computing device 204, this is meant as merely exemplary. Alternatively, any number of imaging devices 201, client computing devices 202, networks 203, or server computing devices 204 may be present. Some or all of the components of imaging device 201, client computing device 202, and/or server computing device 204 may be combined into a single device with or without the use of a network 203. Likewise, some or all of the components of imaging device 201, client computing device 202, and/or server computing device 204 may be separated into distinct devices connected through the network 203 or other connection methods. Some or all of the steps 101-107 in FIG. 1 may alternatively be performed by one or more client computing devices 202 with or without the use of a network 203.

The various devices depicted in FIG. 2 may comprise computing devices or reside on computing devices such as servers, desktop computers, laptop computers, tablet computers, personal digital assistants (PDA), smartphones, mobile phones, smart devices, appliances, sensors, or the like. Computing devices may comprise processors, memories, network interfaces, peripheral interfaces, and the like.

The various devices in FIG. 2 may be configured to communicate directly or indirectly with a wireless network such as through a base station, a router, switch, or other computing devices. In an embodiment, the components may be configured to utilize various communication protocols such as Global System for Mobile Communications (GSM), General Packet Radio Services (GPRS), Enhanced Data GSM Environment (EDGE), Code Division Multiple Access (CDMA), Wideband Code Division Multiple Access (WCDMA), Bluetooth, High Speed Packet Access (HSPA), Long Term Evolution (LTE), and Worldwide Interoperability for Microwave Access (WiMAX).

The devices may be further configured to utilize user datagram protocol (UDP), transport control protocol (TCP), Wi-Fi, satellite links and various other communication protocols, technologies, or methods. Additionally, the devices may be configured to connect to an electronic network without communicating through a wireless network. The devices may be configured to utilize analog telephone lines (dial-up connection), digital lines (T1, T2, T3, T4, or the like), Digital Subscriber lines (DSL), Ethernet, or the like. It is further contemplated that the devices may be connected directly to a computing device through a USB port, Bluetooth, infrared (IR), Firewire port, thunderbolt port, ad-hoc wireless connection, or the like. Devices may be configured to send, receive, and/or manage messages such as email, SMS, IM, MIMS, or the like.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method of assessing collateral ventilation in a lung of a patient, the method comprising:
    analyzing computerized tomography data of a lung, wherein analyzing the computerized tomography data comprises:
        segmenting the lung into separate lobes;
        segmenting at least one of the separate lobes into a plurality of lung segments;
        calculating emphysema scores for one or more regions of each of the plurality of lung segments based on a density mask;
        identifying a fissure defect;
        identifying one or more lung segments of the plurality of lung segments adjacent to the fissure defect;
        calculating a fissure defect score based on a size of the fissure defect;
        determining a proximity of the fissure defect to the one or more regions of the one or more identified lung segments;
        selecting a lung segment of the one or more identified lung segments; and
        determining whether collateral ventilation is present or above a threshold level in the selected lung segment based on the calculated emphysema scores for the one or more regions of the selected lung segment, fissure defect score, and the proximity of the fissure defect to the one or more regions of the selected lung segment.

2. The method of claim 1, wherein collateral ventilation is determined to be present or above a threshold level if the one or more regions of the selected lung segment has an emphysema score above a threshold emphysema score value, that the fissure defect has a fissure defect score above a threshold fissure defect score value, and that the proximity of the fissure defect to the one or more regions of the selected lung segment is within a threshold proximity.

3. The method of claim 1, wherein determining whether collateral ventilation is present or above a threshold level in the selected lung segment is further based on which fissure comprises the fissure defect, where on the fissure the fissure defect is located, or which of the plurality of lung segments the fissure defect separates.

4. The method of claim 1, further comprising:
    identifying airways, wherein determining whether collateral ventilation is present or above a threshold level in the selected lung segment is based on whether an airway is identified within a threshold proximity to the one or more regions of the selected lung segment.

5. The method of claim 1, further comprising:
    identifying airways, wherein determining whether collateral ventilation is present or above a threshold level in the selected lung segment is based on whether an airway is identified within a threshold proximity to the fissure defect.

6. The method of claim 1, further comprising:
    calculating a collateral ventilation score for the selected lung segment based on the calculated emphysema scores for the one or more regions of the selected lung segment, fissure defect score, and proximity of the fissure defect to the one or more regions of the selected lung segment, wherein determining whether collateral ventilation is present or above a threshold level in the selected lung segment is based on the calculated collateral ventilation score.

7. The method of claim 6, further comprising:
    determining a degree of collateral ventilation based on the calculated collateral ventilation score.

8. The method of claim 1, further comprising:
    creating a report indicating one or more lung segments of the plurality of lung segments determined to have collateral ventilation or degrees of collateral ventilation for the one or more lung segments.

9. The method of claim 8, wherein the report comprises one or more potential treatment sites and one or more suggested implantable devices for the one or more potential treatment sites to cause lung volume reduction or reduce hyperinflation, wherein the selected lung segment is determined not to have collateral ventilation or a degree of collateral ventilation below a threshold level and at least one potential treatment site of the one or more potential treatment sites is an airway leading to the selected lung segment.

10. The method of claim 8, wherein the report comprises one or more potential treatment sites and one or more suggested therapeutic agents or implantable devices to be delivered to the one or more potential treatment sites to cause lung volume reduction or reduce hyperinflation, wherein the selected lung segment is determined to have collateral ventilation or a degree of collateral ventilation above a threshold level and at least one potential treatment site of the one or more potential treatment sites comprises the one or more regions within the selected lung segment.

11. The method of claim 8, wherein the report comprises one or more potential treatment sites and one or more suggested therapeutic agents or implantable devices to be delivered to the one or more potential treatment sites to minimize collateral ventilation between the one or more lung segments of the plurality of lung segments, wherein the selected lung segment is determined to have collateral ventilation or a degree of collateral ventilation above a threshold level and at least one potential treatment site of the one or more potential treatment sites comprises an airway leading to the fissure defect.

12. A method of assessing collateral ventilation in a lung of a patient, the method comprising:
    analyzing computerized tomography data of a lung, wherein analyzing the computerized tomography data comprises:
        segmenting the lung into separate lobes;
        segmenting at least one of the separate lobes into a plurality of lung segments;
        identifying a fissure defect;
        identifying one or more lung segments of the plurality of lung segments adjacent to the fissure defect;
        calculating emphysema scores for one or more regions of a first lung segment of the one or more lung segments adjacent to the fissure defect and for one or more regions of a second lung segment of the one or more lung segments adjacent to the fissure defect on an opposing side of the fissure defect based on a density mask;
        calculating a fissure defect score based on a size of the fissure defect;
        determining proximity of the fissure defect to the one or more regions of the first lung segment and the one or more regions of the second lung segment; and
        determining whether collateral ventilation is present or above a threshold level in the first or second lung segment based on the calculated emphysema scores, fissure defect score, and the proximity the fissure defect to the one or more regions of the first and second lung segments.

13. The method of claim 12, wherein collateral ventilation is determined to be present or above a threshold level if the one or more regions of the first lung segment has a first emphysema score above a threshold emphysema score value, the one or more regions of the second lung segment has a second emphysema score above the threshold emphysema score value, the fissure defect has a fissure defect score above a threshold fissure defect score value, the proximity of the fissure defect to the one or more regions of the first lung segment is within a threshold proximity, and the proximity of the fissure defect to the one or more regions of the second lung segment is within the threshold proximity.

14. The method of claim 12, further comprising:
Calculating a collateral ventilation score for the first or second lung segments based on the calculated emphysema scores of the one or more regions of the first and second lung segments, fissure defect score, and proximity the fissure defect to the one or more regions of the first and second lung segments, wherein determining whether collateral ventilation is present or above a threshold level in the first or second lung segments is based on the calculated collateral ventilation score.

15. The method of claim 14, further comprising:
determining a degree of collateral ventilation based on the calculated collateral ventilation score.

16. The method of claim 12, further comprising:
creating a report indicating one or more lung segments of the plurality of lung segments determined to have collateral ventilation or degrees of collateral ventilation for the one or more lung segments.

17. The method of claim 16, wherein the report comprises one or more potential treatment sites and one or more suggested implantable devices for the one or more potential treatment sites to cause lung volume reduction or reduce hyperinflation, wherein the first or second lung segment is determined not to have collateral ventilation or a degree of collateral ventilation below a threshold level and at least one potential treatment site of the one or more potential treatment sites is an airway leading to the first or second lung segment.

18. The method of claim 16, wherein the report comprises one or more potential treatment sites and one or more suggested therapeutic agents or implantable devices to be delivered to the one or more potential treatment sites to cause lung volume reduction or reduce hyperinflation, wherein the first or second lung segment is determined to have collateral ventilation or a degree of collateral ventilation above a threshold level and at least one potential treatment site of the one or more potential treatment sites comprises the one or more regions within the first or second lung segment.

19. The method of claim 16, wherein the report comprises one or more potential treatment sites and one or more suggested therapeutic agents or implantable devices to be delivered to the one or more potential treatment sites to minimize collateral ventilation between the one or more lung segments, wherein the first or second lung segment is determined to have collateral ventilation or a degree of collateral ventilation above a threshold level and at least one potential treatment site of the one or more potential treatment sites comprises an airway leading to the fissure defect.

* * * * *